United States Patent [19]

Watson et al.

[11] 4,226,988
[45] Oct. 7, 1980

[54] N-SUBSTITUTED PARAMENTHANE CARBOXAMIDES

[75] Inventors: Hugh R. Watson, Wargrave; David G. Rowsell, Staines; David J. Spring, Datchet, all of England

[73] Assignee: Wilkinson Sword Limited, London, England

[21] Appl. No.: 4,332

[22] Filed: Jan. 18, 1979

Related U.S. Application Data

[60] Division of Ser. No. 796,973, May 16, 1977, Pat. No. 4,150,052, which is a continuation of Ser. No. 486,566, Jul. 8, 1974, abandoned, which is a continuation-in-part of Ser. No. 221,755, Jan. 28, 1972, abandoned.

[30] Foreign Application Priority Data

Feb. 4, 1971 [GB] United Kingdom ............... 3928/71
Feb. 4, 1971 [GB] United Kingdom ............... 3934/71

[51] Int. Cl.³ .................. C07D 295/18; C07D 213/75
[52] U.S. Cl. ........................... 544/176; 260/326.5 E; 544/391; 546/226; 546/309; 424/248.53; 424/250; 424/263; 424/267; 424/274

[58] Field of Search ............... 260/326.5 E; 546/226, 546/309; 544/176, 386, 391

[56] References Cited

U.S. PATENT DOCUMENTS

| | | | |
|---|---|---|---|
| 3,046,274 | 7/1962 | Böhme et al. | 546/176 |
| 3,296,306 | 1/1967 | Doering et al. | 546/226 |
| 4,137,305 | 1/1979 | Rowsell et al. | 546/226 |
| 4,150,052 | 4/1979 | Watson et al. | 546/226 |

OTHER PUBLICATIONS

Rowsell et al., Chem. Abs. 80:52286u (1974).
Kato et al., Chem. Abs. 72:90648f (1970).
Geigy et al., Chem. Abs. 48:9610i (1954).

*Primary Examiner*—Mary C. Lee
*Attorney, Agent, or Firm*—Leydig, Voit, Osann, Mayer & Holt, Ltd.

[57] ABSTRACT

Novel compounds are disclosed having a physiological cooling action on the skin. The compounds are N-substituted p-methane 3-carboxamides.

1 Claim, No Drawings

N-SUBSTITUTED PARAMENTHANE CARBOXAMIDES

RELATED APPLICATIONS

This application is a division of U.S. Application Ser. No. 796,973, filed May 16, 1977, now U.S. Pat. No. 4,150,052, issued Apr. 17, 1979, which was a continuation of U.S. Application Ser. No. 486,566, filed July 8, 1974 (abandoned), which was a continuation-in-part of U.S. Application Ser. No. 221,755, filed Jan. 28, 1972 (abandoned).

FIELD OF INVENTION

This invention relates to compounds having a physiological cooling effect on the skin and on the mucous membranes of the body, particularly those of the mouth, nose, throat and gastrointestinal tract.

BACKGROUND OF THE INVENTION AND PRIOR ART

Menthol is well known for its physiological cooling effect on the skin and mucous membranes of the mouth and has been extensively used as a flavouring agent (menthol being a major constituent of oil of peppermint) in foodstuffs, beverages, dentifrices, mouthwashes, etc. and as a component in a wide range of toiletries, liniments and lotions for topical application. Menthol is also a well known tobacco additive for producing a "cool" sensation in the mouth when smoking.

It is well established that the "cooling" effect of menthol is a physiological effect due to the direct action of menthol on the nerve endings of the human body responsible for the detection of hot or cold and is not due to latent heat of evaporation. It is believed that the menthol acts as a direct stimulus on the cold receptors at the nerve endings which in turn stimulate the central nervous system.

Although menthol is well established as a physiological coolant its use, in some compositions, is circumscribed by its strong minty odour and its relative volatility.

A few other compounds have been reported in the technical literature as having an odour of flavour similar to menthol and from time to time have been proposed as flavourants or odourants in a variety of topical and ingestible compositions. For example, Japanese Patent Publication No. 39-19627 reports that 3-hydroxymethyl p-menthane (menthyl carbinol) has a flavour closely resembling that of 1-menthol and suggests its use as a flavourant in confectionery, chewing gum and tobacco. In Swiss Patent No. 484,032 certain saccharide esters of menthol are proposed as additives to tobacco. In French Patent Specification No. 1,572,332 N,N-Dimethyl 2-ethylbutanamide is reported as having a minty odour and refreshing effect, and the minty odour of N,N-diethyl 2,2-dimethylpropanamide is referred to. A similar effect is reported for N,N-diethyl 2-ethylbutanamide in Berichte 39, 1223, (1906). A minty odour has also been reported for 2, 4, 6-trimethylheptan-4-ol and 2,4,6-trimethyl hept-2-en-4-ol in Parfums-Cosmetiques-Savons, May 1956, pp. 17–20. The cooling effect of menthol and other related terpene alcohols and their derivatives has also been studied and reported in Koryo, 95, (1970), pp. 39–43. 2,3-p-menthane diol has also been reported as having a sharp cooling taste (Beilstein, Handbuch der Organischen Chemie, 4th Ed. (1923) Vol. 6, p. 744.).

Despite this knowledge of other compounds having an odour and flavour similar to that of menthol, menthol is still extensively used in topical, ingestible and other compositions notwithstanding the disadvantages mentioned above, namely its very strong odour and its relative volatility.

OBJECTS OF THE INVENTION

It is an object of the present invention to provide other compounds having a pronounced physiological cooling effect, in many cases far more persistent than that obtained with menthol, without the attendant disadvantages of a strong odour.

It is a further object to provide compounds having a pronounced physiological cooling effect and being of relatively low volatility.

SUMMARY OF INVENTION

According to the present invention there is provided a novel group of 3-substituted-p-menthanes which have a pronounced physiological cooling activity, which have little or no odour, which are of relatively low volatility and which are substantially non-toxic. These compounds are 3-substituted-p-menthanes of the formula:

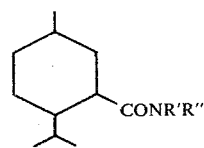

I where
- R', when taken separately, is hydrogen or an aliphatic radical containing up to 25 carbon atoms;
- R", when taken separately is hydroxy, or an aliphatic radical containing up to 25 carbon atoms, with the proviso that when R' is hydrogen R" may also be an aryl radical of up to 10 carbon atoms and selected from the group consisting of substituted phenyl, phenalkyl or substituted phenalkyl, naphthyl and substituted naphtbyl, pyridyl; and
- R' and R", when taken together with the nitrogen atom to which they are attached, represent a cyclic or heterocyclic group of up to 25 carbon atoms, e.g. piperidino, morpholino etc.

In the above definitions "aliphatic" is intended to include any straight-chained, branched-chained or cyclic radical free of aromatic unsaturation, and thus embraces alkyl, cycloalkyl, alkenyl, cycloalkenyl, alkynyl, hydroxyalkyl, acyloxyalkyl, alkoxy, alkoxyalkyl, aminoalkyl, acylaminoalkyl, carboxyalkyl and similar combinations.

Typical values for R' and R" when aliphatic are methyl, ethyl, propyl, butyl, isobutyl, n-decyl, cyclopropyl, cyclohexyl, cyclopentyl, cycloheptylmethyl, 2-hydroxyethyl, 3-hydroxy-n-propyl, 6-hydroxy-n-hexyl, 2-aminoethyl, 2-acetoxyethyl, 2-ethylcarboxyethyl, 4-hydroxybut-2-ynyl, carboxymethyl etc.

When R" is aryl typical values are benzyl, naphthyl, 4-methoxyphenyl, 4-hydroxyphenyl, 4-methylphenyl, 3-hydroxy-4-methylphenyl, 4-fluorophenyl, 4-nitrophenyl, 2-hydroxynaphthyl, pyridyl, etc.

DETAILED DESCRIPTION

The 3-substituted-p-menthanes used as cold receptor stimulants of the invention may be readily prepared by conventional methods, such as by the reaction of the corresponding acid chloride (obtained by reacting p-menthane-3-carboxylic acid with thionyl chloride) with the appropriate amine. The reaction will usually be carried out in solution in the presence of a hydrogen chloride receptor e.g. sodium hydroxide. The reaction proceeds smoothly at room temperature.

The compounds used as cold receptor stimulants in accordance with this invention exhibit both geometric and optical isomerism and, depending on the starting materials and the methods used in their preparation the compounds may be isomerically pure, i.e. consisting of one geometric or optical isomer, or they may be isomeric mixtures, both in the geometric and optical sense.

As is well known, the basic p-menthane structure is a chair-shaped molecule which can exist in cis or trans forms. Substitution of the carboxyl or amide group into the 3-position gives rise to four configurational or geometric isomers depending upon whether the substitution is axially or equatorially into the cis or trans isomer, the four isomers being related as menthol is to neomenthol, isomenthol, and neoisomenthol. In general it is found that in the compounds used in this invention the equatorially substituted derivatives have the greater cooling effect than the axial compounds and are to be preferred.

Substitution of the amide group in the 3-position of the p-menthane structure also gives rise to optical isomerism, each of the above-mentioned four geometric isomers, existing in d, l and dl forms. The physiological cooling effect is found, in most cases, to be greater in the l-form than in d-form, and in some cases substantially greater. The amide derivative of the l-acid are therefore preferred.

The cooling sensation created by the compounds used in this invention on the skin and mucous membranes, for example, in the mouth, varies both in intensity and longevity from compound to compound.

When either R' and R" is aliphatic their preferred values are $C_1-C_9$ straight or branched chain alkyl, $C_1-C_9$ straight or branched chain hydroxyalkyl or aminoalkyl and $C_1-C_1$ acylated derivatives thereof, and $-C_nH_{2n}COH'''$ or $-C_nH_{2n}COOR'''$, where $-C_nH_{2n}$ is a straight or branched chain alkylene radical in which n is an integer of from 1-6 and R''' is hydrogen or a $C_1-C_8$ alkyl or hydroxyalkyl group, preferably a $C_1-C_4$ straight chain alkyl group.

In general the monosubstituted compounds, i.e. where R' is H, are preferred although di-substituted compounds where R' and R" are both $C_1-C_3$ alkyl also show a very pronounced cooling effect. Most preferred of all are compounds where R' is H and R" is $C_1-C_3$ alkyl, $C_1-C_4$ hydroxyalkyl, or $-CH_2COOR'''$, where R''' is $C_1-C_4$ alkyl.

Also included within the scope of this invention are compounds where R' is H and R" is hydroxy or substituted phenyl, e.g. alkylphenyl, hydroxyphenyl, alkoxyphenyl, halophenyl of up to 10 carbon atoms, phenalkyl or substituted phenalkyl e.g. benzyl, naphthyl or substituted naphthyl, and compounds where R' and R" are joined to form a cyclic group. When so joined R' and R" preferably represent an alkylene chain, optionally interrupted by oxygen, which together with the nitrogen atom to which R' and R" are attached forms a 5- or 6-membered heterocyclic ring.

For the purposes of the present disclosure the following test procedure has been devised as a means to identify compounds having a physiological cooling activity in accordance with the present invention and herein referred to as cold receptor stimulants. This test is intended purely as a means for identifying compounds having a physiological cooling activity and useful in the present invention and for giving an indication of the different relative activities of the compounds, as between themselves and as compared with menthol, when applied in a particular manner to a particular part of the body. The results are not necessarily indicative of the activity of these compounds in other formulations and other parts of the body where other factors come into play. For example, a controlling factor in the onset of cooling effect, its intensity and longevity will be the rate of penetration of the compounds through the epidermis and this will vary in different locations on the human body. The formulation of actual products according to this invention will therefore be done largely on an empirical basis although the test results and other figures given herein will be useful as a guide, particularly in the formulation of products for oral administration, since the test procedure to be described involves oral application of the compound. A similar test may, of course, be devised for the purposes of measuring the relative activities of the compounds on another area of the body, for example, the face or forearm, and this will be a useful guide in the choice of compounds to be used in preparations for external topical usage.

It will also be noted that the described test procedure is done on a statistical basis. This is necessary since sensitivity to these compounds will vary not only from compound to compound and from one part of the body to another, but also from one individual to another. Tests of this nature are commonly used in the testing of the organoleptic properties, e.g. taste, smell etc. of organic and inorganic compounds, see Kirk-Othmer: Encyclopedia of Chemical Technology, 2nd. Ed. (1967) Vol. 14 pages 336-344.

TEST PROCEDURE

The following test procedure is aimed at determining the minimum quantity of the test compound required to produce a noticeable cooling effect on a person of average sensitivity, this minimum quantity being termol the threshold for that particular compound. The tests are carried out on a selected panel of 6 people of median sensitivity to l-menthol.

PANEL SELECTION

To select a test panel of average sensitivity the following procedure is used. Known quantities of l-menthol in solution in petroleum ether (bp. 40-60) are placed on 5 mm. squares of filter paper, whereafter the solvent is allowed to evaporate. A panel of observers is enrolled and asked to place one impregnated square at a time on the tongue and to report on the presence or absence of a cooling effect. The quantity of l-menthol on each impregnated square is gradually reduced from a value substantially above 0.25 $\mu$g. per square to substantially below 0.25 $\mu$g, the precise range being immaterial. Conveniently, one starts with squares containing 2.0 $\mu$g. l-menthol, the amount on each successive square being half that of the preceding square, i.e. the second test square will contain 1.0 $\mu$g, the third 0.5 $\mu$g and so on. Each quantity is tested on the tongue at least 10 times. In this way, the thresholds to cold receptor stimulus by 1-menthol are determined for each individual of the panel, the threshold for each individual being that amount of 1-menthol for which, in a series of not less than 10 test applications, a cooling effect is reported 50% of the time. Six panel members are now selected whose threshold to 1-menthol is in the range 0.1 μg to 10 μg and whose average threshold is approximately 0.25 μg., this select panel being regarded as the test panel of average sensitivity.

COMPOUND TESTING

To test the activity of compounds according to this invention, the above procedure is repeated using only the 6 selected panel members of average sensitivity to 1-menthol. The individual thresholds for each test compound on each of the 6 selected panel members are determined and averaged. Those compounds whose average threshold on the select test panel is 100 μg or less are regarded as having cooling activity in accordance with this invention.

TEST RESULTS

The following table sets out the relative cooling activities of compounds of the formula defined above when tested according to the foregoing procedure.

Table

| Compound | | Threshold μg. | mp./bp. °C. |
|---|---|---|---|
| R' | R'' | | |
| N | —$CH_3$ | 1.1 | mp.95°–97° |
| " | —$C_2H_5$ | 0.3 | mp.82.5°–84.5° |
| " | —$C_3H_7(n)$ | 0.8 | mp.65°–67° |
| " | —$C_3H_7(iso)$ | 0.5 | mp.94°–96° |
| " | —$C_4H_9(n)$ | 1.4 | mp.88°–90° |
| " | —$C_4H_9(iso)$ | 0.9 | mp.111°–112° |
| " | —$C_4H_9(sec)$ | 0.7 | mp.116°–119° |
| " | —$C_4H_9(tert.)$ | 0.4 | mp.145°–146° |
| " | —$C_5H_{11}(n)$ | 3 | mp.80°–82° |
| " | —$C_{10}H_{21}(n)$ | 10 | bp.176–8/0.25 mm |
| " | —$CH_2CH_2OH$ | 5 | bp.160°/0.1 mm |
| " | —$(CH_2)_3OH$ | 3 | bp.170°/0.1 mm |
| " | —$CH_2CH(OH)CH_3$ | 5.5 | bp.184°/0.1 mm |
| " | —$C(CH_3)_2CH_2OH$ | 0.4 | mp.123° |
| " | —$CH_2CHCCH_2OH$ | 17 | bp.180°/0.1 mm |
| " | —$(CH_2)_6OH$ | 1.0 | bp.220°/0.1 mm |
| " | —$CH(C_2H_5)CH_2OH$ | 1.0 | bp.190°/0.1 mm |
| " | —$CH_2OH$ | 12 | mp.141°–142° |
| " | —$CH_2COOC_3H_7(n)$ | 0.3 | bp.170°/0.1 mm |
| " | —$CH_2COOC_2H_5$ | 0.2 | bp.150°/0.1 mm |
| " | —$CH_2COOH$ | 16 | mp.93–96 |
| " | —$CH(CH_3)COOC_2H_5$ | 0.4 | bp.160°/0.1 mm |
| " | —$CH_2CH_2COOC_2H_5$ | 1.5 | bp.152°/0.1 mm |
| " | —$CH_2COOCH_3$ | 0.6 | bp.130°–140°/0.1 mm |
| " | —$CH(CH_3)CH_2COOC_2H_5$ | 0.8 | bp.164°/0.1 mm |
| " | —$CH_2CH_2OCOCH_3$ | 1.5 | bp.159°–162°/0.1 mm |
| " | —$CH_2CH_2NH_2$ | 20 | |
| —$CH_3$ | —$CH_3$ | 1.5 | bp.56°–57°/0.1 mm |
| —$C_2H_5$ | —$C_2H_5$ | 3 | bp.78°–80°/0.1 mm |
| —$CH_2CH_2OH$ | —$CH_2CH_2OH$ | 50 | |
| —$CH_3$ | —$CH_2CO_2C_2H_5$ | 0.8 | bp.125–8/0.2 mm |
| —$CH_3$ | —$CH_2CH_2OH$ | 5 | bp.140/0.2 mm |
| —$C_3H_7(iso)$ | —$CH_2CH_2OH$ | 3 | bp.125–30/0.05 mm |
| H | —$C_3H_5(cyclo)$ | 0.5 | mp.125–6 |
| " | —$C_5H_9(cyclo)$ | 0.5 | mp.105–7 |
| " | —$C_6H_{11}(cyclo)$ | 1 | mp.170–2 |
| " | —$C_7H_{13}(cyclo)$ | 3 | mp.161–3 |
| —$C_2H_5$ | —$C_4H_9(iso)$ | 5 | bp.84°–87°/0.1 mm |
| H | —$CH_2(C_7H_{13})(cyclo)$ | 20 | bp.170°–174°/0.1 |
| H | —OH | 11 | mp.124°–125° |
| —$(CH_2)_4$— | | 5 | mp.54°–56° |
| —$(CH_2)_5$— | | 6 | bp.102–104/0.5 mm |
| | —$CH_2CH_2OCH_2CH_2$— | 5.5 | bp.101°–103°/0.5 mm |
| | —$CH_2CH_2NHCH_2CH_2$ | 15 | |
| | —$CH(CH_3)CH_2CH_2CH(CH_3)$— | 0.5 | bp.102/0.005 mm |
| | —$CH_2(CH_3)CH_2CH_2CH_2CH(CH_3)$— | 2 | bp.130/0.01 mm |
| | —$CH(CH_3)CH(C_2H_5)CH_2C(CH_3)$— | | |
| | —$CH(iso-C_3H_7)CH_2CH_2CH(CH_3)CH_2CH_2$— | 50 | mp.87°–91° |
| H | —$CH_2PH$ | 10 | mp.106°–107° |
| " | —$C_6H_4CMe(p)$ | 0.1 | mp.177 |
| " | —$C_6H_4OH(p)$ | 1.4 | bp.230°/0.1 mm |
| | —$C_6H_4Me(p)$ | 0.3 | mp.176–8 |
| | —$C_6H_4OH(o)$ | 0.5 | mp.123–4 |
| | —$C_6H_3Me(p)OH(m)$ | 0.1 | mp.183–4 |
| | —$C_6H_3Me_2(m,p)$ | 0.1 | mp.106–7 |
| | —$C_6H_4P(p)$ | 0.5 | mp.125 |
| | —$C_6H_4NO_2(p)$ | 0.3 | mp.134–8 |
| | —3-Pyridyl | 0.5 | bp.175/0.1 mm |

UTILITY

The compounds of this invention find utility in a wide variety of consumer products for consumption by or application to the human body. Broadly speaking, these products can be divided into comestible and topical compositions, both terms being taken in their broadest possible sense. Thus comestible is to be taken as including not only foodstuffs and beverages taken into the mouth and swallowed, but also other orally ingested compositions taken for reasons other than their nutritional value, e.g. indigestion tablets, antacid preparations, laxatives etc. Comestible products are also to be taken to include edible compositions taken by mouth, but not necessarily swallowed, e.g. chewing gum. Topical compositions are to be taken as including not only compositions such as perfumes, powders and other toileteries, lotions, liniments, oils and ointment applied to the external surfaces of the human body, whether for medical or other reasons, but also compositions applied to, or which, in normal usage, come in contact with, internal mucous membranes of the body, such as those of the nose, mouth, or throat, whether by direct or indirect application or inhalation, and thus include nasal and throat sprays, dentifrice, mouthwash and gargle compositions. Topical compositions are also to be taken to include toilet articles such as cleansing tissues and toothpicks.

A further class of compositions into which the compounds of this invention can usefully be incorporated are tobacco and associated articles e.g. pipe and cigarette filters, especially filter tips for cigarettes.

Compounds according to this invention are illustrated by the following Examples. All temperatures are given in degrees Centigrade. The p-menthane-3-carboxylic acid used as starting material in all the Examples was itself prepared by the carbonation of the Grignard reagent derived from l-menthol according to known techniques.

EXAMPLE 1

PREPARATION OF N-ETHYL p-MENTHANE-3-CARBOXAMIDE p-Menthane-3-carboxylic acid (1.84 g.), was heated under reflux with thionyl chloride (4 ml.) for 3 hours. The excess of thionyl chloride was then distilled off in vacuo. The crude product p-menth-3-oyl chloride was dissolved in diethyl ether (25 ml.) and the ethereal solution was added with stirring and cooling to a solution of ethylamine (1.0 ml. of 70% w/s solution in water) and sodium hydroxide (0.4 g.) in water (25 ml.). The mixture was stirred for one hour and the ethereal layer was then separated. The aqueous layer was washed with ether (25 ml.) and the combined ethereal solution was washed with dilute hydrochloric acid and then water. The ether solution was dried (MgSO$_4$) and evaporated to give a white crystalline solid. This solid was recrystallised from acetone: water (9:1) by dissolving the crystals at room temperature and then cooling to produce N-ethyl-p-menthane-3-carboxamide as a white crystalline solid, mp. 82.5°–84.5°.

[] $D^{25}$ = −46.71° (concentration—2.14 gms. per 100 ml. in ethanol)

EXAMPLE 2

PREPARATION OF N-p-MENTH-3-OYLGLYCINE ETHYL ESTER

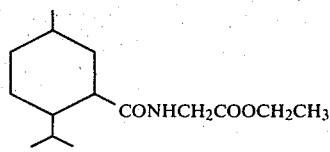

Sodium bicarbonate (8.4 g., 0.1 mole) and glycine ethyl ester hydrochloride (7 g. 0.05 mole) were dissolved in water (100 ml.), and a solution of p-menth-3-oyl chloride (10 g., 0.05 mole) in ether (50 ml.) was added and the mixture stirred vigorously at room temperature for 2 hours. At the end of this time the other layer was separated and dried (MgSO$_4$). Removal of the solvent left an oily solid (12.3 g.) This was distilled under reduced pressure to yield N-p-menth-3-oylglycine ethyl ester, bp. 150°–2°/0.1 mm. as a colourless liquid which rapidly solidified.

EXAMPLE 3

PREPARATION OF N-(2-HYDROXYETHYL)-p-MENTHANE-3-CARBOXAMIDE

A solution of p-menth-3-oyl chloride prepared as in Example 1 (4.0 g., 0.020 moles) in chloroform (30 ml.) was added dropwise to a stirred solution of ethanolamine (3 g., 0.043 moles) in chloroform (50 ml.). The reaction mixture becomes warm, goes cloudy and finally a yellow oil starts to separate out. After stirring for 2 hours at room temperature the mixture was poured into water. The organic layer was separated, washed with dilute H$_2$SO$_4$, and dried (MgSO$_4$). Removal of the solvent left a viscous oil (3.8 g.). This was distilled under vacuum to yield N-(2-hydroxyethyl)-p-menthane-3-carboxamide as a colourless very viscous oil, b.p. 160°/01. mm.

EXAMPLE 4

PREPARATION OF N-(3-HYDROXYPROPYL)-p-MENTHANE-3-CARBOXAMIDE

The procedure of Example 3 was repeated using propanolamine in place of the ethanolamine. N-(3-hydroxypropyl)-p-menthane-3-carboxamide was obtained as a very viscous oil, b.p. 170°/0.1 mm. EXAMPLE 5

PREPARATION OF N,N-DIMETHYL-p-MENTHANE-3-CARBOXAMIDE

A mixture of p-methane-3-carboxylic acid (1.84 g.) and thionyl chloride (5 ml.) was heated under reflux for 2 hours. The excess of thionyl chloride was then removed in vacuo. The residue was dissolved in dry diethyl ether (25 ml.) and this solution was added slowly with stirring and cooling to a solution of dimethylamine (0.46 g.) and sodium hydroxide 0.4 g.) in water (25 ml.). After stirring at room temperature for 1 hour, the ether layer was separated and the aqueous layer was extracted with a further quantity (25 ml.) of ether. The combined ether extracts were dried (MgSO$_4$) and evaporated to leave an oil. This oil was distilled to give N,N-dimethyl-p-menthane-3-carboxamide as a colourless oil, b.p. 56°–7°/0.01 mm.

EXAMPLE 6

PREPARATION OF N,N-BIS(2-HYDROXYETHYL)-p-MENTHANE-3-CARBOXAMIDE

A solution of p-menth-3-oyl chloride (4.0 g., 0.020 moles) in chloroform (30 ml.) was added dropwise to a stirred solution of diethanolamine (4.2 g., 0.044 moles) in chloroform (50 ml.). The reaction mixture goes cloudy and a yellow oil separates out. After 2 hours at room temperature, the yellow oil (upper layer) was separated. Infra red spectographic analysis indicated this to be $(HOCH_2CH_2)_2 NH_2^+Cl^-$. Removal of the chloroform left a viscous oil (6 g.). Thin layer chromatography ($CHCl_3$ and $CHCl_3 + 10\% CH_3OH$) indicated it to consist of one major component and a minor component of larger $R_f$ value. This was separated by column chromatography on neutral alumina (activity 1). Eluting with chloroform (200 ml.) removed the minor component and the major product was eluted from the column with chloroform + 5% methanol. The major component was shown to be N,N-bis(2-hydroxyethyl)-p-menthane-3-carboxamide.

Analysis: Found C: 65.8; H: 10.6; N: 5.2. Calculated C: 66.4; H: 10.7; N: 5.2.

EXAMPLE 7

PREPARATION OF N-p-MENTH-3-OYLGLYCINE n-PROPYL ESTER

Following the procedure of Example 2 p-menth-3-oyl chloride (2.0 g., 0.01 moles), was reacted with glycine propyl ester hydrochloride (1.5 g., 0.01 moles) and sodium bicarbonate (1.6 g., 0.02 moles). The crude product was distilled b.p. 170°/0.1 mm. (After distillation the product rapidly solidifies). (Found, C: 68.2; H: 1016; N: 5.0. $C_{16}H_{29}NO_3$ requires, C: 67.8; H: 10.6; N: 4.9.)

EXAMPLE 8

PREPARATION OF N-(2-HYDROXY-n-PROPYL)p-MENTHANE-3-CARBOXAMIDE p-Menth-3-oyl chloride (3.0 g.) was reacted with isopropanolamine (3.0 g.) according to the procedure of Example 3. The product, N-(2-hydroxy-n-propyl)-p-menthane-3-carboxamide, was obtained as a viscous oil, boiling point: 184°/0.1 mm.

EXAMPLE 9

PREPARATION OF N-(1,1-DIMETHYL-2-HYDROXYETHYL)-p-MENTHANE-3-CARBOXAMIDE p-Menth-3-oyl chloride (3.0 g.) was reacted with 2-amino-2-methyl-propan-1-ol (3.0 g.) according to the procedure of Example 3. Product N-(1,1-dimethyl-2-hydroxyethyl)-p-menthane-3-carboxamide was obtained as a crystalline solid which was recrystallised from aqueous methanol. M.p. 123°.

EXAMPLE 10

PREPARATION OF N,N-DIETHYL-p-MENTHANE-3-CARBOXAMIDE

Following the procedure of Example 5, p-menthane-3-carboxylic acid (1.84 g.) was reacted with thionyl chloride and the p-menth-3-oyl chloride then reacted with diethylamine (0.74 g.) in the presence of sodium hydroxide (0.4 g.). The product N,N-diethyl-p-menthane-3-carboxamide was recovered.

EXAMPLE 11

PREPARATION OF N-TERT-BUTYL-p-MENTHANE-3-CARBOXAMIDE

Following the procedures of Example 1, p-menthane-3-carboxylic acid (1.84 g.) was reacted with thionyl chloride and the crude p-menth-3-oyl chloride recovered and reacted with tert butylamine (0.74 g.) in the presence of sodium hydroxide (0.4 g.). The crystalline product, N-tert-butyl-p-menthane-3-carboxamide, was recovered and recrystallised from aqueous ethanol. M.p. 145°–146°.

EXAMPLE 12

PREPARATION OF N-METHYL-p-MENTHANE-3-CARBOXAMIDE

The procedures of Example 1 were repeated using methylamine (0.32 g.) in place of the ethylamine. Crystalline product N-methyl-p-methane-3-carboxamide was recovered, M.p. 95°–97°.

EXAMPLE 13

PREPARATION OF N-(p-MENTH-3-OYL) MORPHOLINE

The procedure of Example 5 was repeated using morpholine (0.88 g.) in place of the dimethylamine. The product N-(p-menth-3-oyl) morpholine was recovered.

EXAMPLE 14

PREPARATION OF p-MENTHANE HYDROXAMIC ACID

Hydroxylamine hydrochloride 1.0 g., (0.014 mole) and sodium bicarbonate 3.4 g (0.04 mole) were dissolved in 30 ml. water in a flask filled with reflux condenser and magnetic stirrer. When evolution of $CO_2$ had ceased 20 ml. of ether was added and the solution stirred vigorously. p-Menth-3-oyl chloride 2 g. (0.001 mole) in 15 ml. of ether, was added dropwise down the condenser.

After all of the acid chloride had been added, spectra were taken of samples of the ether layer, at 15 minute intervals. When the characteristic acid chloride absorption at 1800 cm$^{-1}$ was no longer present in the spectra the reaction was complete. The ether layer was carefully separated from the aqueous layer, and evaporated to dryness, yielding 2 g. of white powder.

The product, p-menthane hydroxamic acid, was recrystallised from an ethanol/water mixture.

EXAMPLE 15

PREPARATION OF N-(4-HYDROXYBUT-2-YNYL)-p-MENTHANE-3-CARBOXAMIDE

Sodium bicarbonate (2.5 g.) and 4-aminobut-2-yn-1-ol hydrochloride (2.5 g.) were dissolved in water (60 ml.) and a solution of p-menth-3-oyl chloride in ether (100 ml.) added. The mixture was stirred vigorously for two hours and the ether layer separated and dried over MgSO$_4$. Evaporation of the ether gave N-(4-hydroxybut-2-ynyl)-p-menthane-3-carboxamide as a very viscous liquid: b.p. 180°/0.1 mm.

EXAMPLE 16

PREPARATION OF N-(p-HYDROXYPHENYL)-p-MENTHANE-3-CARBOXAMIDE p-Menth-3-oyl chloride (2.0 g.) and p-aminophenol (2.2 g.) were stirred for four hours at room temperature in ether (100 ml.). Product N-(p-hydroxyphenyl)-p-menthane-3-carboxamide was recovered.

We claim:

1. Substantially odorless, non-volatile physiologically active cooling compounds of the formula

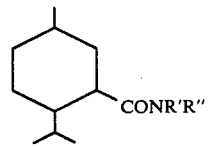

where R' and R", when taken together jointly represent a straight or branched chain alkylene group having a total of up to 10 carbon atoms, said alkylene group providing a chain of 4 or 5 carbon atoms the opposite ends of which are attached to the nitrogen atom to form a 5 or 6 membered heterocycle; a —CH$_2$CH$_2$OCH$_2$CH$_2$— group, or a CH$_2$CH$_2$NHCH$_2$CH$_2$ group;

or, when taken separately, R' represents hydrogen and R" represents a pyridyl group.

* * * * *

UNITED STATES PATENT AND TRADEMARK OFFICE
CERTIFICATE OF CORRECTION

PATENT NO. : 4,226,988

DATED : October 7, 1980

INVENTOR(S) : Hugh R. Watson et al.

It is certified that error appears in the above—identified patent and that said Letters Patent is hereby corrected as shown below:

Title page, line 3 of the Abstract "p-methane" should read --p-menthane--.

Column 1, line 46, "of" should read --or--.

Column 3, line 47, "$C_1-C_1$" should read --$C_1-C_4$--.

Column 3, line 48, "$C_nH_{2n}COH'''$" should read --$C_nH_{2n}COR'''$--.

Column 4, line 48, "termol" should read --termed--.

In the table below columns 5 and 6, lines 20 through 42, "N" should read --H--.

In the table, line 31, "$-CH_2CHCCH_2OH$" should read ---$CH_2C \equiv CCH_2OH$--.

In the table, line 59, "$CH_2PH$" should read --$CH_2Ph$--.

In the table, line 60, "$C_6H_4CMe(p)$" should read --$C_6H_4OMe(p)$--.

In the table, line 66, "$C_6H_4P(p)$" should read --$C_6H_4F(p)$--.

Column 8, lines 52 and 53, "EXAMPLE 5" should be set off as a separate paragraph (see EXAMPLE 1, 2, etc.).

UNITED STATES PATENT AND TRADEMARK OFFICE
CERTIFICATE OF CORRECTION

PATENT NO. : 4,226,988
DATED : October 7, 1980
INVENTOR(S) : Hugh R. Watson et al.

It is certified that error appears in the above-identified patent and that said Letters Patent is hereby corrected as shown below:

Column 8, line 58, "p-methane-3-carboxylic" should read --p-menthane-3-carboxylic--.

Column 10, line 35, "N-methyl-p-methane-3-carboxamide" should read --N-methyl-p-menthane-3-carboxamide--.

Signed and Sealed this

Twenty-fourth Day of February 1981

[SEAL]

Attest:

RENE D. TEGTMEYER

Attesting Officer

Acting Commissioner of Patents and Trademarks